US00PP16485P2

(12) United States Plant Patent
Talmadge

(10) Patent No.: US PP16,485 P2
(45) Date of Patent: Apr. 25, 2006

(54) ***NEMESIA* PLANT NAMED 'BALAROYAL'**

(50) Latin Name: *Nemesia foetans*
Varietal Denomination: Balaroyal

(75) Inventor: Paul A. Talmadge, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 47 days.

(21) Appl. No.: 11/022,605

(22) Filed: Dec. 27, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Nemesia* plant named 'Balaroyal' characterized by its deep purple-colored flowers with yellow "eye", medium green-colored foliage, and upright and spreading growth habit.

1 Drawing Sheet

Latin name of genus and species of plant claimed: *Nemesia foetans.*
Variety denomination: 'Balaroyal'.

BACKGROUND OF THE INVENTION

The present invention relates to a new and distinct cultivar of *Nemesia* plant, botanically known as *Nemesia foetans,* and hereinafter referred to by the cultivar name 'Balaroyal'.

The new cultivar originated in a controlled breeding program in Guadalupe, Calif. during the spring of 2002. The objective of the breeding program was the development of *Nemesia* cultivars with a well-branched, spreading growth habit, unique flower colors, and continuous flowering.

The female (seed) parent of 'Balaroyal' was the proprietary *Nemesia foetans* selection designated 2113-1-4-3, not patented, characterized by its light pink-colored flowers and well-branched habit. The male (pollen) parent of 'Balaroyal' was the proprietary *Nemesia foetans* selection designated 2068-2-3-1, not patented, characterized by its deep blue-colored flowers, average branching habit, and late blooming time. The new cultivar was discovered and selected by the inventor as a single flowering plant within the progeny of the above stated cross-pollination during the autumn of 2002 at Guadalupe, Calif.

Asexual reproduction of the new cultivar by terminal stem cuttings since the autumn of 2002 at Guadalupe, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balaroyal' as a new and distinct cultivar of *Nemesia* plant:

1. Deep purple-colored flowers with yellow "eye".
2. Medium green-colored foliage.
3. Upright and spreading growth habit.

Plants of the new cultivar differ from plants of the female parent primarily in flower color and from plants of the male parent primarily in flower color.

Of the *Nemesia* cultivars known to the inventor, the most similar to the new cultivar is 'Balartublu', U.S. Plant patent application Ser. No. 10/734,859. However, in side by side comparisons, plants of the new cultivar differ from plants of 'Balartublu' in the following characteristics:

1. Plants of the new cultivar have larger leaves than plants of 'Balartublu'.
2. Plants of the new cultivar have lighter, brighter flower color than plants of 'Balartublu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of 'Balaroyal'. The plants were grown in 10 cm pots for 9 weeks in a greenhouse at West Chicago, Ill.

DETAILED BOTANICAL DESCRIPTION

Figure 1:
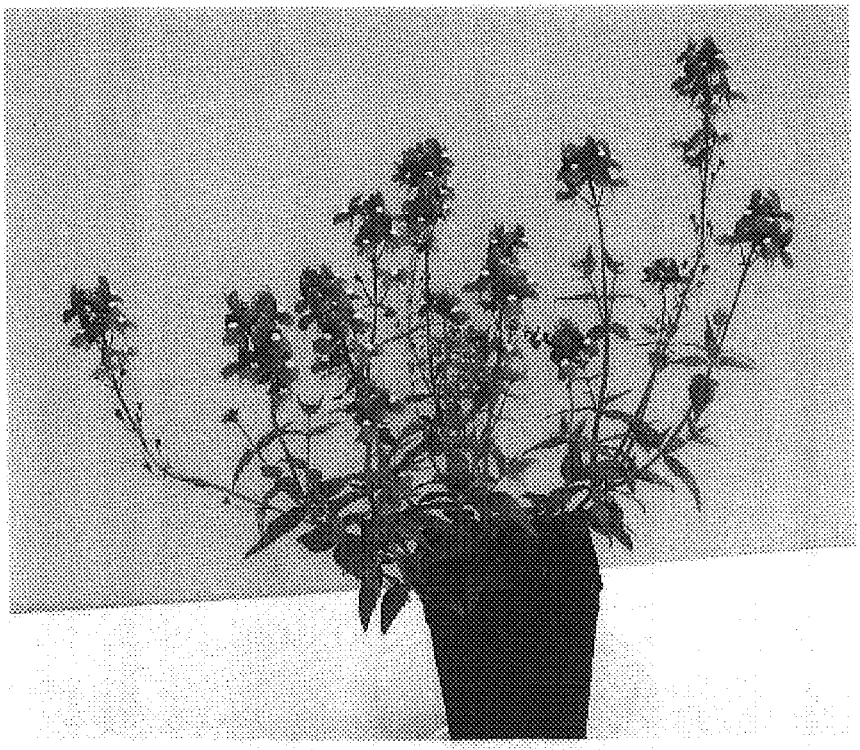
FIG. 1 illustrates the overall growth habit of the new cultivar.
Figure 2:
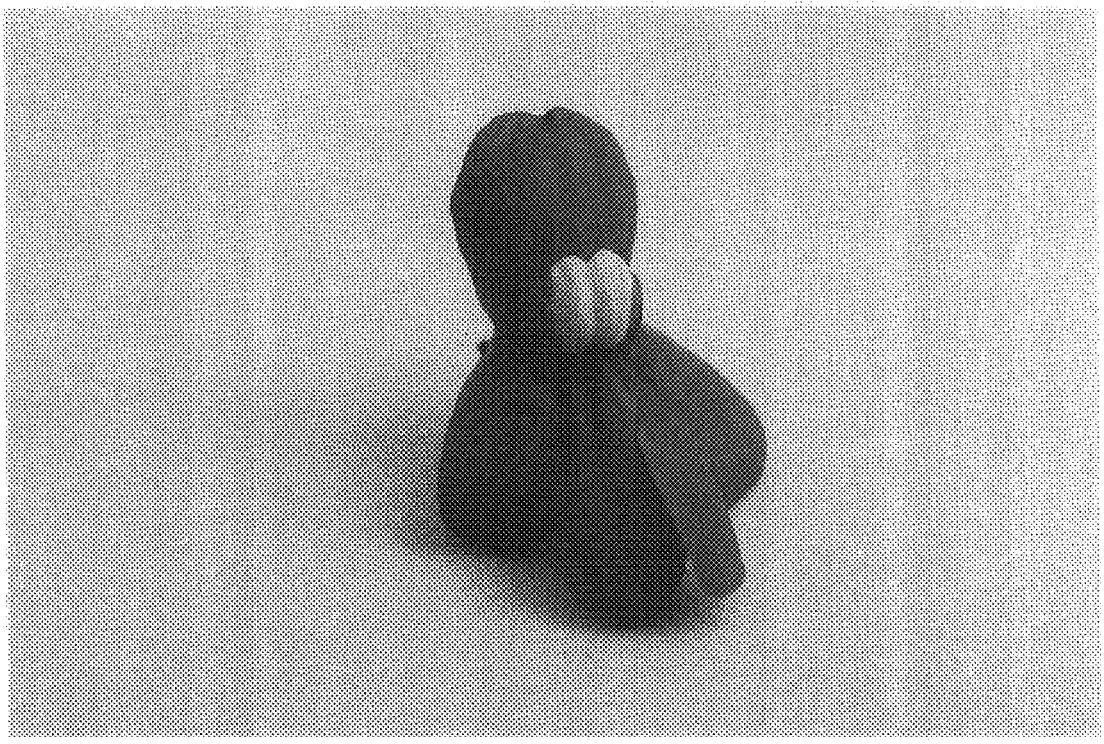
FIG. 2 illustrates a close-up view of an individual flower of the new cultivar.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 24, 2004 between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown in 10 cm pots for 9 weeks while utilizing a soil-less growth medium. Greenhouse temperatures were maintained at approximately 65° to 75° F. (18° to 24° C.) during the day and approximately 50° to 60° F. (10° to 15° C.) during the night. Daytime greenhouse light levels were maintained at approximately 4,000 to 7,000 foot-candles.

Botanical classification: *Nemesia foetans,* cultivar Balaroyal.

Parentage:

*Female (seed) parent.*—Proprietary *Nemesia foetans* selection designated 2113-1-4-3, not patented.

*Male (pollen) parent.*—Proprietary *Nemesia foetans* selection designated 2068-2-3-1, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fine and fibrous.

*Rooting habit.*—Branching.

Plant description:

*Crop time.*—Approximately 5–7 weeks from a rooted cutting.

*Habit of growth.*—Moderately vigorous with good branching.

*Form.*—Upright and outwardly spreading.

*Size.*—Height from soil level to top of foliage: Approximately 17.7 cm. Diameter (area of spread): Approximately 37.6 cm.

*Branch.*—Quantity: Approximately 3 main branches with secondary branches from every node. Strength: Moderate. Shape: Square in cross section. Appearance: Wiry. Length of main branch: Approximately 28.3 cm. Diameter of main branch: Approximately 2 mm. Texture of all branches: Puberulent. Color of all branches: 144A. Internode length at middle of main branch: Approximately 2.5 cm.

*Foliage.*—Quantity per branch: Approximately 10. Fragrance: Slight. Type: Simple. Arrangement: Opposite. Orientation to stem: Right angle. Shape: Ovate. Apex: Broadly acute. Base: Obtuse. Margin: Serrate. Venation pattern: Palmate. Length of leaf taken from middle of branch: Approximately 2 cm. Leaf width: Approximately 7 mm. Texture of upper and lower surfaces: Glabrous. Color of mature foliage: Upper surface: 146A with venation of 144B. Lower surface: 146B with venation of 144B.

Flowering description:

*Time to first flower.*—Approximately 7 weeks from a rooted cutting.

*Flowering habit.*—Freely flowering under outdoor growing conditions with substantially continuous blooming from spring through autumn and year round in greenhouse environment.

Inflorescence description:

*Type.*—Terminal clusters.

*Size.*—Length/depth: Approximately 4.2 cm. Width/diameter: Approximately 3.3 cm.

*Number per plant.*—Approximately 19 fully open racemes and 7 developing racemes.

*Number of fully open flowers per raceme at any one time.*—Approximately 8.

Flower description:

*Type.*—Solitary, zygomorphic, and bilabiate with nectar spur. Flowering is acropetally toward apex. Flowers are persistent and not fragrant.

*Flower size.*—Length: Approximately 2.7 cm. Width: Approximately 1.4 cm. Depth, including nectar spur: Approximately 7 mm.

*Aspect.*—Facing outward or upward.

*Petals.*—Quantity: Five per flower. The upper four petals are fused at base forming a lip having two central linear lobes and one outer obovate lobe on each side. The lower petal has two obovate lobes and is modified into a nectar spur. All lobes have rounded tips and entire margins. Spur length: Approximately 7 mm. Spur diameter at base: Approximately 2.1 mm. Spur diameter at tip: Approximately 1 mm. Spur texture: Glabrous. Spur color: 22C with overlay at tip of N80A.

*Petal color.*—Upper surface of mature lobes: N87A with palate of 1A. Lower surface of mature lobes: N87C.

*Peduncle.*—Shape: Square in cross section. Strength: Strong, wiry. Angle to the stem: Slightly acute. Length: Approximately 4.1 cm. Diameter: Approximately 1 mm. Texture: Moderately pubescent. Color: 144A.

*Pedicel.*—Strength: Good. Angle to stem: Acute. Length: Approximately 7 mm. Diameter: Approximately 1 mm. Texture: Dense short, soft, glandular pubescence. Color: Darker than N144D.

*Bud.*—Shape: Ovoid with spur. Length: Approximately 3 mm. Diameter: Approximately 3.6 mm. Texture: Glabrous. Color: 83C.

*Calyx.*—Shape: Star. Width: Approximately 6.2 mm. Formed by five sepals fused at base. Sepal shape: Elliptic. Sepal margin: Entire. Sepal apex: Acute. Sepal length: Approximately 3.5 mm. Sepal width: Approximately 1 mm. Sepal texture: Upper and lower surfaces: Pubescent. Sepal color: Both surfaces: 137C.

*Reproductive organs.*—Androecium: There are 4 stamens per flower wrapped around pistil. Stamen length: 2 are 4 mm in length and 2 are 3 mm in length. Anther shape: Oval. Anther length: 8 mm. Anther color: 11C. Amount of pollen: Abundant. Pollen color: 14A. Gynoecium: Number: One pistil per flower. Pistil length: 2.3 mm. Stigma length: 1 mm. Stigma color: 15C. Style length: 1 mm. Style color: N155B. Ovary diameter: 1.2 mm. Ovary color: N144D.

Seed and fruit production: Neither seed nor fruit production has been observed.

Disease and pest resistance: Resistance to pathogens and pests common to *Nemesia* has not been observed.

What is claimed is:

1. A new and distinct cultivar of *Nemesia* plant named 'Balaroyal', substantially as herein shown and described.

* * * * *